United States Patent [19]

Goodheart et al.

[11] Patent Number: 5,354,269

[45] Date of Patent: Oct. 11, 1994

[54] METHOD FOR TREATING CANCER RESECTIONS

[75] Inventors: Clyde R. Goodheart, Lincolnshire; Ralph H. Silverman, Morton Grove; M. Satya Murthy, Glenview; Edward F. Scanlon, Northbrook, all of Ill.

[73] Assignee: Fibrogenex, Inc., Morton Grove, Ill.

[21] Appl. No.: 811,269

[22] Filed: Dec. 20, 1991

[51] Int. Cl.$^5$ .................. A61M 31/00; A61K 37/02
[52] U.S. Cl. ............................. 604/49; 514/8
[58] Field of Search ............... 514/8, 12, 2, 56; 424/85.91, 426, 423, 195.1; 604/49, 890

[56] References Cited

U.S. PATENT DOCUMENTS

| | | | |
|---|---|---|---|
| 4,642,111 | 2/1987 | Sakamoto et al. | 604/890 |
| 4,728,637 | 3/1988 | Silverman | 514/8 |
| 4,849,406 | 7/1989 | Salonen | 514/8 |
| 4,918,165 | 4/1990 | Soll et al. | 530/391 |
| 5,112,805 | 5/1992 | Salonen | 514/8 |
| 5,128,321 | 7/1992 | Murray et al. | 514/12 |
| 5,141,958 | 8/1992 | Crozier-Willi et al. | 514/558 |
| 5,246,708 | 9/1993 | von Borstel et al. | 424/450 |
| 5,262,403 | 11/1993 | Nicolson et al. | 514/56 |
| 5,266,327 | 11/1993 | Agrez | 424/426 |
| 5,270,300 | 12/1993 | Hunziker | 514/12 |

Primary Examiner—David Isabella
Attorney, Agent, or Firm—Laff, Whitesel, Conte & Saret, Ltd.

[57] ABSTRACT

A method for preparing fibronectin and further a process for treating cancer resections which prevents or reduces local recurrences of cancer in procedures in which cancerous tissues are resected comprising the steps of: mixing a pharmaceutical fibronectin with a suspending medium to provide a fibronectin composition; applying the fibronectin composition to a surgically exposed tissue from the cancer resection; and closing the surgically exposed tissue using conventional suturing techniques.

20 Claims, No Drawings

METHOD FOR TREATING CANCER RESECTIONS

This invention was made with U.S. Government support under Grant #1R43CA53859-01 that was awarded by the National Cancer Institute of the National Institute of Health. The U.S. Government has certain rights in the invention.

FIELD OF THE INVENTION

This invention relates to a method for treating cancer resections. More particularly, this invention relates to a method for treating cancer resections that involves applying a pharmaceutical complex to wounded or injured tissues at a surgical operative site to prevent or reduce local recurrences of cancer in procedures in which cancerous tissues are resected.

BACKGROUND OF THE INVENTION

U.S. Pat, No. 4,728,637 (Silverman) discloses a pharmaceutical protein complex which includes fibronectin for treating humans and animals with degenerative diseases. The complex disclosed in U.S. Pat. No. 4,728,637 or alternatively, a pure fibronectin composition, is used in the method of the invention herein to treat cancer resections.

The aforementioned fibronectin complex which may be used in the inventive process herein comprises macromolecules produced from human and animal cultured cells, i.e. mesenchymal cells. The mesenchymal cell macromolecular complex used in this invention consists of fibronectin, with or without the macromolecules selected from procollagen, proteoglycan, elastin, laminin and mixtures thereof. As discussed in U.S. Pat. No. 4,728,637, fibronectin and procollagen are part of the compositions of that patent. Whether or not proteoglycan, laminin or elastin are present in the patent composition depends on the particular mesenchymal cell culture used to prepare the complex of the patent.

For purposes of simplification, the above composition of U.S. Pat. No. 4,728,637 is referred to as PROFIPEL TM. It is to be understood that this covers those instances where the composition contains all five ingredients—fibronectins, procollagens, proteoglycans, laminins and elastins; four ingredients—fibronectins, procollagens, proteoglycans, and either elastins or laminins; three ingredients—fibronectins, procollagens and proteoglycans, or the two ingredients, fibronectins and procollagens.

The macromolecules extracted from cultured mesenchymal cells, the PROFIPEL TM, function with each other in consort and not individually. Therefore, they must not be considered as individual ingredients but must be considered as a complex of mesenchymal macromolecules.

The type of mesenchymal cells used to produce PROFIPEL TM can vary. Although it is not required, it is believed that for the treatment of a specific cancer resection, it would be best to prepare PROFIPEL TM from that type of mesenchymal tissue which is beneath the resection. For example, if the cancerous tissue is lung tissue, then the PROFIPEL TM used to treat the cancer resection is preferably collected from cultured lung mesenchymal cells, although any suitable cells may be used to prepare a pharmaceutically acceptable form of fibronectin. Thus, the source of fibronectin may be homologous, heterologous or autologous.

Postoperative recurrence of cancer locally in the incision site is a major problem with the surgical treatment of cancer. Local recurrence predominantly occurs in the central scar and under the skin graft. For instance, chest wall recurrence after radical mastectomy for breast cancer occurs in 10 to 15% of the patients (Cancer 20:1051-1053, 1967; Cancer 57:1421-1425, 1986; J. Surg Oncol 30:149-151, 1985; Arch Surg 111:323-325, 1976). The prognostic significance of local recurrence is ominous, with 3.9% and 0% survival after 5 and 10 years, respectively (Cancer 20:1051-1053, 1967). Depending on the site and type of cancer, local recurrences occur in 5% to 60% of patients undergoing surgical treatment for other kinds of cancer. Research scientists have formulated the hypothesis that such recurrences are due to facilitated lodgement, and subsequent growth, of cancer cells from the patients' circulation at the surgical wound area (Cancer 20:23-30, 1967; J Surg Oncol 30:33-45, 1985; Ann Surg 168:887-890, 1968; Cancer Res 12:929-932, 1959; Cancer 28:545-552, 1971). Local recurrence may also result from inadequate removal of the cancer, i.e., due to leaving cancer cells in the operative site. Similar problems occur in veterinary medicine. In veterinary surgical treatment of animals for cancer, local recurrences may occur for the same reasons as in humans.

SUMMARY OF THE INVENTION

Accordingly, it is an object of the present invention to provide a novel process for treating cancer resections.

It is another object of the present invention to provide a novel process for treating cancer resections which reduces or prevents local recurrences of the cancer.

It is another object of the present invention to provide a novel process for treating cancer resections that may be directly applied to the surgically exposed tissues prior to suturing.

It is yet another object of the present invention to provide a novel process for treating cancer resections which does not interfere with surgical procedures.

The objectives and advantages of the present invention are achieved, in a preferred embodiment, by providing a method that involves applying a pharmaceutical composition of fibronectin to surgically wounded tissues at the operative site in cancer surgery to reduce or prevent local recurrences of the cancer. This is accomplished by initially mixing the fibronectin with a gel material or other liquid suspending or solubilizing agent. Subsequently, the above mixture is applied to the surface of the exposed tissues and the wound is then closed by conventional suturing techniques. Any appropriate suspending or solubilizing liquid or gel may be used that is compatible with the fibronectin composition and which is acceptable for direct application to surgically exposed tissues.

DETAILED DESCRIPTION OF THE INVENTION

The present invention contemplates applying a pharmaceutical complex to wounded or injured tissues at a surgical operative site. In the preferred embodiment, the fibronectin or PROFIPEL TM is prepared from the same species as the species on which it is to be used. For operations on human, preferably fibronectin or PROFIPEL TM is prepared from human cells because it is more potent than cross-species fibronectin or PROFIPEL ™.

The preparation of PROFIPEL ™ is described in detail in U.S. Pat. No. 4,728,637 and that disclosure is incorporated herein in its entirety. Therefore, the present invention provides applying a fibronectin composition to the surgically exposed tissue from a cancer resection wherein the fibronectin composition comprises cellular fibronectin and further includes macromolecules selected from the group consisting of proteoglycans, laminuns, elastins and mixtures thereof.

The substantially pure fibronectin we use in the following examples was prepared as follows:

EXAMPLE 1

Foreskins were obtained from newborns circumcised in a hospital nursery. The foreskins were transported to the laboratory in tissue culture medium containing penicillin and streptomycin at a concentration of 10,000 units/mL and 10 mg/mL, respectively. Each foreskin was minced with sterile scissors into pieces less than 1 mm in diameter, and stirred in trypsin solution (0.25% of trypsin 1:250 in phosphate buffered saline containing 0.02% EDTA (ethylenediamine tetraacetic acid) and no calcium or magnesium salts) at room temperature for 45 minutes to dissociate the cells. The cells were collected by gentle centrifugation, resuspended in 20 mL of MCDB 202 tissue culture medium supplemented with fetal bovine serum (10%), and placed in 4 60×15 mm style tissue culture petri dishes. The cultures were incubated at 36° C. in a humidified incubator flushed with 5% $CO_2$ in air. The medium was changed after a week's incubation, and the cells had formed a complete monolayer after ten days' incubation. However, it is possible to incubate the cells for a much shorter time period, e.g. for one day. The cells were removed from the surface of the culture vessel by rinsing first with EDTA solution (described above) and then treating with the trypsin solution described above. The cells were transferred to plastic roller bottles (In Vitro Scientific Products, Inc., Ventura, Calif., 2x Bottle, area 1780 cm²), at a split ratio of 4:1 based on relative surface areas, using 100 mL/bottle of the same growth medium described above. In five more days of incubation, the cells had completely covered the surface of the roller bottle, and were split once more as before.

After the cells had again formed a confluent sheet, the medium was replaced with production medium (100 mL/bottle). This medium was standard medium 199, obtained from a commercial source as a dry powder and reconstituted with tissue culture grade distilled water according to manufacturer's instructions. The following ingredients were added to the 199: lactalbumin hydrolysate 5g/L; sodium bicarbonate, 2.2 g/L; HEPES buffer, free acid, 0.794 g/L; HEPES buffer, sodium salt, 1.735 g/L; penicillin 100,000 units/L; streptomycin 0.1 g/L; glucose 3 g/L; insulin 10 mg/L; dexamethasone 20 μg/L; solution containing essential amino acids, obtained commercially from Sigma Chemical Co., St. Louis, catalog #M7020, 20 mL/L; solution containing nonessential amino acids, obtained commercially from Sigma Chemical Co., catalog #M7145, 10 mL/L. References herein to production medium are to be understood as referring to the medium described above, although variations on the medium are contemplated. The first production medium was left on the cells for two days to eliminate fetal bovine serum remaining from the growth medium. However, it should be noted that the cells may be exposed to the production medium for less time, e.g. for approximately two hours. It was then discarded and replaced with fresh production medium. This medium was harvested from the cells every two days and replaced with fresh production medium.

Because of the well known susceptibility of cellular fibronectin to degradation by proteases, the fibronectin was purified from each batch of medium harvested from the cells as soon as possible on the same day it was harvested, using the following procedure that permitted purification in minimum time. The medium was filtered through a fiberglass filter to remove any cells or cell debris that might be present. The 600 mL of harvest was pumped through an affinity chromatography column containing a bed of gelatin-agarose, at about 280 mL/hour. Except for a small sample for testing, the medium was discarded after passing through the column. The column bed was flushed with equilibration buffer (sodium phosphate 10 mM, sodium chloride 150 mM, pH 7.2) until the absorption at 280 nm had returned to baseline. Elution buffer (Tris basic 50 mM, urea 4 M, pH 7.5) was pumped through the column to elute the fibronectin from the affinity bed. A single sharp absorptive peak was collected in fractions 7, 8 and 9. These were pooled and passed through a G-25 column equilibrated with water to remove the urea. A broad peak was collected in fractions 9 through 11, containing 5.43 mg of protein in 28 mL. This was filtered through a sterile 0.2 μm filter for sterilization after adding 3.6 mL of concentrated phosphate buffer, so that after lyophilization, the reconstituted freeze-dried product would contain 1 mg/mL of fibronectin, 0.05 M phosphate buffer, pH 7.5, 0.1 M NaCl. It was then dispensed aseptically into sterile vials to contain 1 mg each, frozen, and lyophilized.

Samples taken during the procedure and after lyophilization were analyzed on PAGE-SDS under reducing conditions. The patterns of bands on the gels indicated that the product was cellular fibronectin with a high degree of purity.

EXAMPLE 2

The process for preparing mouse cellular fibronectin was essentially the same as that described above in Example 1 for human cellular fibronectin. Mouse embryos were obtained from Strain A mice in about the 16th day of gestation, when they were about 1.2 cm long. They were removed from the uterus and membranes, decapitated, eviscerated, and minced into pieces smaller than 1 mm diameter. The tissue was trypsinized as described above for human newborn foreskins. After centrifugation, the cells from five embryos were dispensed into two plastic roller bottles in medium MCDB 202 supplemented with 10% fetal bovine serum. After a week of growth, the cells were transferred to eight new bottles using the same medium.

After the cells became confluent, the medium was changed to production medium. The first harvest was discarded after two days. Every two days after that, mouse cellular fibronectin was purified from the medium as described in Example 1. In one such harvest of 700 mL, the fibronectin eluted from the affinity column in fractions 7, 8 and 9. This was desalted by passing through a G-25 column, with the peak in fractions 9, 10, and 11. After sterilization, the final yield was 7.28 rag. Analysis on PAGE-SDS under reducing conditions revealed a tight cluster of bands at the same position as the human cellular fibronectin and at a slightly higher molecular weight position than the commercial bovine plasma fibronectin used as a marker.

EXAMPLE 3

A wedge of liver is surgically resected in a group of Strain A mice by electrocautery. Subsequently, 100,000 of the TA3Ha continuous line of experimental tumor cells were injected into the tail vein. Prior to injection, the cells had been treated by mixing them with solutions of various concentrations of bovine plasma fibronectin purchased from commercial sources or human or mouse cellular fibronectins prepared according to Examples 1 and 2 and allowing them to stand for one hour at room temperature. The results are shown in Table 1.

TABLE 1

| | Number of animals with tumors at 14 days | | | | |
|---|---|---|---|---|---|
| Treatment | n | Lung | P | Surgical Liver[a] | P |
| Control | 240 | 129 (54%) | | 107 (45%) | |
| Bovine pFN[b] | 34 | 8 (24%) | NS[d] | 5 (15%) | NS |
| Human cFN[c] | 48 | 17 (35%) | NS | 11 (23%) | NS |
| Mouse cFN | 73 | 15 (21%) | NS | 7 (10%) | <.005 |

[a]Surgical liver = that part of the liver that was operated upon
[b]pFN = plasma fibronectin
[c]cFN = cellular fibronectin
[d]NS = not significant; chi-square test used throughout These results show that fibronectin from bovine plasma decreased the percentage of animals with implants in either the lungs or the liver. Both the cellular fibronectin from a different species (human) and from the same species (mouse) reduced the incidence of metastatic implants, but the same-species material did so about twice as effectively as the cross-species material. In the experiments in Table 1, the incidence of metastatic implants in the surgically injured liver treated with mouse cellular fibronectin dropped from 45% to 10% as a result of the treatment, and the difference was statistically significant. A similar decrease of implants occurred in the lungs, which is the only organ that develops a significant number of tumors in unoperated animals when the cells are injected in the tail vein. In this instance, the action of the fibronectin was on the cells, since they were exposed to the fibronectin prior to being injected.

EXAMPLE 4

In this example, the surgically exposed tissue surface is treated by topically applying the fibronectin or PROFIPEL TM to the exposed tissue surface. This treatment is exemplified in Example 4, wherein Strain A mice were first operated upon by making a wedge resection of the liver by electrocautery, as in Example 3. The cut surface of the liver was treated topically by painting the cauterized surface with a solution of 1.0 mg of fibronectin in 1 mL of Ora-Plus gel (purchased from Paddock Labs, Minneapolis, Minn.). The wounded liver was replaced in the abdominal cavity, and the peritoneum and skin were closed with appropriate sutures. 100,000 TA3Ha cells were injected into the tail vein, and the animals were examined by autopsy 14 days later. The results are shown in Table 2.

TABLE 2

Effect of topical application of mouse cellular fibronectin on development of local metastatic tumor implants

| | n | Surgical Liver | P |
|---|---|---|---|
| Untreated control mice | 240 | 107 (47%) | |
| Treated with control gel | 29 | 12 (41%) | NS |
| Treated with mouse cFN gel | 35 | 4 (11%) | <.05 |

In the experiment of Example 4, the control gel, i.e., suspending agent without fibronectin, did not decrease the percentage of animals with metastatic implants compared to the untreated control mice. When mouse cellular fibronectin was included in the gel, however, and applied topically to the cauterized surface of the liver, there was a statistically significant decrease in the percentage of animals that developed implants at the site of injury in the liver. In some of the individual experiments that were grouped in Table 2, there were no implants in any of the experimental animals. Thus, the percentage of animals with implants is expected to decrease as technique improves.

This inventive method is not limited to surgical procedures performed by electrocautery. This procedure was used in the examples described herein. However, the inventive method herein will be useful in any type of surgery, whether performed by cutting, by blunt dissection, by electrocautery, by laser, by freezing, or by any other method.

In summary, the preferred mode of the invention for use in human surgery is to paint the solution of human cellular fibronectin on the surfaces of any tissues incised or injured during the surgery. This preference is not intended to limit the invention to human use, nor to use only of cellular fibronectin, nor to the homologous (same species) source of the fibronectin, nor to application by painting.

Variations on the preferred mode are contemplated. Fragments of the fibronectin molecules can be synthetically prepared by cleaving the molecules at selected sites with specific proteolytic enzymes. Some fractions may be more active than the intact molecules. Fragments identified as particularly active may be able to be synthesized. Further, the essence of the invention is that the fibronectin or PROFIPEL TM be applied topically to the exposed tissue. Whether this is done by painting a solution of substantially pure fibronectin, PROFIPEL TM, or other fibronectin compositions, on the tissue, or by spraying it on, or by irrigating or washing it across the surface, or by some other means is not the important feature. Although, for illustrative purposes, Ora-Plus was used; however, other gels or suspending solutions could equally well be used, including such a gel further containing an agent or agents to protect the active protein from degradation.

The foregoing is for purposes of illustration, rather than limitation of the scope of protection accorded this invention. The latter is to be measured by the following claims, which should be interpreted as broadly as the invention permits.

The invention claimed is:

1. A process for treating cancer resections which prevents or reduces local recurrences of cancer in procedures in which cancerous tissues are resected comprising the steps of:
mixing a pharmaceutical fibronectin with a suspending medium to provide a fibronectin composition;

applying said fibronectin composition to a surgically exposed tissue from a cancer resection; and closing the surgically exposed tissue using conventional suturing techniques.

2. The process of claim 1 wherein the pharmaceutical fibronectin is a substantially pure fibronectin.

3. The process of claim 1 wherein the pharmaceutical fibronectin is a fibronectin complex.

4. The process of claim 1 wherein the pharmaceutical complex comprises macromolecules which are derived from a culture medium of cells selected from a group consisting of animal and human mesenchymal cells and wherein the complex of macromolecules comprises both fibronectins and procollagens.

5. The process of claim 4 wherein the macromolecules further include proteoglycans.

6. The process of claim 4 wherein the macromolecules further include macromolecules selected from the group consisting of proteoglycans, laminins, elastins and mixtures thereof.

7. The process of claim 1 wherein the suspending medium is a gel.

8. The process of claim 1 wherein said mixture may be applied to said exposed tissue by irrigation.

9. The process of claim 1 wherein said mixture may be applied by spraying onto said exposed tissue.

10. The process of claim 1 wherein said mixture may be applied by painting on said exposed tissue.

11. The process of claim 1 wherein the resected cancerous tissue may be human.

12. The process of claim 1 wherein the resected cancerous tissue may be animal.

13. The process of claim 1 wherein the pharmaceutical complex is a protein.

14. The process of claim 13 wherein the protein is lyophilized.

15. The process of claim 2 wherein the fibronectin may be prepared by cleaving its molecules at selected sites with at least one proteolytic enzyme.

16. The process of claim 2 wherein the fibronectin is heterologous.

17. The process of claim 2 wherein the fibronectin is homologous.

18. The process of claim 2 wherein the fibronectin is autologous.

19. A process of treating cancer resections which prevents or reduces local recurrences of cancer in procedures in which cancerous tissues are resected comprising the steps of:

mixing a pharmaceutical complex of macromolecules with a suspending medium, said complex of macromolecules are derived from a culture medium of cells selected from a group consisting of animal and human mesenchymal cells and wherein the complex of macromolecules comprises both fibronectins and procollagens;

applying said mixture to a surgically exposed tissue from a cancer resection; and closing the surgically exposed tissue using conventional suturing techniques.

20. A process of treating cancer resections which prevents or reduces local recurrences of cancer in procedures in which cancerous tissues are resected comprising the steps of:

mixing a pharmaceutical complex of macromolecules with a suspending medium, said complex of macromolecules are derived from a culture medium of cells selected from a group consisting of animal and human mesenchymal cells and wherein the complex of macromolecules comprises substantially pure fibronectin;

applying said mixture to a surgically exposed tissue from the cancer resections; and closing the surgically exposed tissue using conventional suturing techniques.

* * * * *